United States Patent [19]
Hosler et al.

[11] 3,997,617
[45] Dec. 14, 1976

[54] 4,9-CIS-1-CYCLOHEXYL-1,3,3-TRIMETHYLHYDRINDANE

[75] Inventors: Peter Hosler, Wallingford; David S. Gates, Swarthmore, both of Pa.

[73] Assignee: Sun Ventures, Inc., St. Davids, Pa.

[22] Filed: Dec. 19, 1975

[21] Appl. No.: 642,224

Related U.S. Application Data

[63] Continuation-in-part of Ser. No. 218,338, Jan. 17, 1972, Pat. No. 3,929,923.

[52] U.S. Cl. .......................... 260/666 PY; 74/200; 260/667; 252/59
[51] Int. Cl.$^2$ .................. C07C 13/28; C07C 13/46
[58] Field of Search ............... 260/666 PY; 252/59

[56] References Cited

UNITED STATES PATENTS

| 2,249,987 | 7/1941 | Stanley et al. | 260/666 PY |
| 2,629,751 | 2/1953 | Wiggins | 260/667 |
| 3,411,369 | 11/1968 | Hamman et al | 74/200 |

*Primary Examiner*—Veronica O'Keefe
*Attorney, Agent, or Firm*—J. Edward Hess; Donald R. Johnson; Paul Lipsitz

[57] ABSTRACT

4,9-Cis-1-cyclohexyl-1,3,3-trimethylhydrindane is a new compound and is a fluid with improved tractive properties.

3 Claims, No Drawings

4,9-CIS-1-CYCLOHEXYL-1,3,3-TRIMETHYLHYDRINDANE

CROSS REFERENCE TO RELATED APPLICATION

This present application is a continuation-in-part of Ser. No. 218,338 filed Jan. 17, 1972.

BACKGROUND OF THE INVENTION

The preparation of 1-cyclohexyl-1,3,3-trimethylhydrindane and the use thereof as a traction fluid is known. See, for example, Hamman et al, U.S. Pat. No. 3,411,369 and Wiggins, U.S. Pat. No. 2,629,751.

In copending application Ser. No. 218,338, now U.S. Pat. No. 3,929,923, it is disclosed that one specific isomer of 1-cyclohexyl-1,3,3-trimethylhydrindane, namely the 4,9-cis isomer, has substantially better traction properties than the other isomers. That application discloses how to make the 4,9-cis isomer in high yield.

SUMMARY OF THE INVENTION

The present invention is 4,9-cis-1-cyclohexyl-1,3,3-trimethylhydrindane as a new composition. It has a much higher coefficient of traction than the other isomers.

DESCRIPTION OF THE INVENTION

The isomers of 1-cyclohexyl-1,3,3-trimethylhydrindane have the following properties:

|  | A | Isomer B | C (4,9 cis-) |
|---|---|---|---|
| Normal Boiling Point* | 578° F | 60° F | 613° F |
| $n_D^{20}$ | 1.5028 | 1.5003 | 1.5045 |
| $d_4^{20}$ | .9303 | .9452 | .9415 |
| ASTM VI | <0 | <0 | 0 |
| VTF VI | −27 | −18 | 0 |
| $KV_{210}$ | 3.26 | 3.67 | 4.13 |
| Coefficient of Traction** | .043 | .0425 | .0445 |

*Normal boiling points calculated from Vapor Pressure Chart. J. B. Maxwell, Data Book on Hydrocarbons, D. Van Nostrand, N. Y. 1950.
**Coefficient is the average specified in Table III footnote 1 of U.S. 3,608,385.

By way of comparison the product of U.S. Pat. No. 3,411,369 (Example 3) had a corresponding density, refractive index, and normal boiling point of 0.944, 1.5055, and 601°–603° F respectively, whereas these values in U.S. Pat. No. 2,629,751 are 0.9365, 1.5035, and 561° F (Example 2).

One skilled in the art will recognize from the above that the 4,9-cis isomer has an unexpectedly higher coefficient of traction than either of the other isomers. Although the absolute difference in the coefficients is not large, it is very significant from a traction standpoint since it is known that relatively small increases in traction coefficient can correspond to relative large increases in the durability of the traction transmission. This is so because the durability in an inverse exponential function of the traction coefficient. Thus, a 10% increase in coefficient may effect a 50% improvement in durability.

The 4,9-cis isomer can be prepared by the hydrogenation of 1-phenyl-1,3,3-trimethylindane which has been found to proceed in a series sequential reaction to compounds A, C and B in that order. By controlling the reaction temperature and time the C isomer can be obtained as the major product. The 1-phenyl-1,3,3-trimethylindane can be obtained by known procedures, see e.g., U.S. Pat. No. 3,411,369.

The following examples illustrate the preparation of our new composition.

EXAMPLE 1

300 ml of molten 1-phenyl-1,3,3-trimethylindane and 15 grams of 58% nickel on kieselguhr were charged to a one-liter stirred pressure reactor. After purging with hydrogen, the reactor was pressured to 1200 psi with hydrogen and held at that pressure for the course of the reaction. Heat was applied through electrical windings, with thermostatic controls to maintain 200° C ± 10° C. Samples were analyzed by UV spectroscopy and gas chromatography at 1, 2, 3, and 6 hours, to determine the approximate amount of each isomer in the reaction product. The results are as follows:

| Time | Percent of A | B | C |
|---|---|---|---|
| 1 | 35 | 5 | 38 |
| 2 | 21 | 8 | 74 |
| 3 | 2 | 7 | 92 |
| 6 | 3 | 7 | 91 |

EXAMPLE 2

A reactor was charged and operated in manner similar to Example 1, except that the temperature was controlled at 250° C., with the results shown below. It is noted that isomer C has a maximum concentration at approximately 2 hours and then is gradually converted to isomer B.

| Time | Percent of A | B | C |
|---|---|---|---|
| 1 | 15 | 5 | 79 |
| 2 | 3 | 10 | 87 |
| 3 | 3 | 20 | 80 |
| 6 | 3 | 46 | 52 |

Runs similar to those in Examples 1 and 2 are listed in the following table with the time for maximum C concentration given:

| Temp., °C | H₂ Pressure psi | Time | Products A | B | C |
|---|---|---|---|---|---|
| 175 | 1200 | 18 | 5 | 2 | 93 |
| 200 | 1200 | 6 | 2 | 6 | 92 |
| 225 | 1200 | 3 | 2 | 8 | 90 |
| 250 | 1200 | 2 | 3 | 13 | 84 |
| 275 | 1200 | 2 | 7 | 24 | 69 |
| 225 | 700 | 6 | 1 | 10 | 89 |

EXAMPLE 3

A reactor was charged and operated in manner similar to Example 1, except Raney nickel was used as a catalyst, with the following results:

| Temp., °C | H₂ Pressure psi | Time | A | Products B | C |
|---|---|---|---|---|---|
| 175 | 1200 | 6 | 70 | 13 | 17 |
| 200 | 1200 | 6 | 2 | 6 | 92 |
| 225 | 1200 | 6 | 21 | 7 | 72 |

-continued

| Temp., °C | H₂ Pressure psi | Time | Products A | B | C |
|---|---|---|---|---|---|
| 250 | 1200 | 6 | 20 | 10 | 64 |

In the experiments above with Raney nickel, the catalyst lost its activity at the higher temperatures, apparently because of the sintering of the nickel surface at high temperatures. The temperature range for this catalyst is narrowly limited to about 200° C.

EXAMPLE 4

A high pressure tubular flow reactor was charged with 4 liters (dry bulk volume) of rhodium on charcoal. The reactor was purged with nitrogen, then purged with hydrogen and pressured to 2500 psi with hydrogen. Temperature in the reactor was maintained at 202° C ± 11° C. 1-phenyl-1,3,3-trimethylindane was diluted with 50% by volume cyclohexane and charged to the top of the reactor at 4 liters per hour. After the reaction, the cyclohexane was removed by distillation and the resulting product was found to contain 1.6% starting material, 16.7% compound B and 81.7% compound C.

EXAMPLE 5

A high pressure tubular flow reactor was charged with 4 liters (dry bulk volume) of 58% nickel on kieselguhr pellets. The reactor was purged with nitrogen, then purged with hydrogen and pressured to 1500 psi with hydrogen. Temperature in the reactor was maintained at 220° C ± 10° C. 1-phenyl-1,3,3-trimethylindane was diluted with 50% by volume cyclohexane and charged to the reactor at 350 ml/hour. After the reaction, the cyclohexane was removed by distillation and the resulting product was found to contain 3% product A, 7% product B, and 90% product C.

It is apparent from the above that the amount of the C isomer in the reaction product mixture can be controlled at almost any desired level. For traction purposes it will obviously be desirable to maximize percentage of C isomer preferably at least 80% most preferably at least 90%. A pure C isomer can of course be obtained by fractionating the product as by distillation, chromotography, and the like. The coefficient of traction will vary depending on the relative proportion of the C isomer, but will be greater than 0.0435 usually greater than 0.0440.

The 4,9-cis isomer can be used as is a traction fluid or as a component thereof, such as a lubricant comprising conventional non-hydrocarbon lube additives (e.g., extreme pressure, antioxidant, antirust, antifoam, antiwear, dispersant) and a hydrocarbon base containing the hydrindane and 0.1–20 parts (based on the hydrindane) of a hydrogenated linear, liquid polymer of isobutylene.

The invention claimed is:

1. 4-9-Cis-1-cyclohexyl-1,3,3-trimethylhydrindane.
2. A traction composition comprising at least 80% of 4-9-cis-1-cyclohexyl-1,3,3-trimethylhydrinadane the balance comprising a hydrocarbon base lubricant, said composition being added having a coefficient of traction of at least 0.0435.
3. An isomer of 1-cyclohexyl-1,3,3-trimethylhydrindane having a density of 0.9415 and a refractive index of 1.5045.

* * * * *